United States Patent
Wang

(10) Patent No.: US 11,129,642 B2
(45) Date of Patent: Sep. 28, 2021

(54) NEEDLE GROOVE BODY, PUNCTURE FRAME BODY AND PUNCTURE FRAME

(71) Applicant: Qin Wang, Jiangsu (CN)

(72) Inventor: Qin Wang, Jiangsu (CN)

(*) Notice: Subject to any disclaimer, the term of this patent is extended or adjusted under 35 U.S.C. 154(b) by 193 days.

(21) Appl. No.: 16/317,952

(22) PCT Filed: Jul. 15, 2016

(86) PCT No.: PCT/CN2016/090134
§ 371 (c)(1),
(2) Date: Jan. 15, 2019

(87) PCT Pub. No.: WO2018/010165
PCT Pub. Date: Jan. 18, 2018

(65) Prior Publication Data
US 2019/0247086 A1      Aug. 15, 2019

(51) Int. Cl.
*A61B 17/34* (2006.01)
*A61B 8/00* (2006.01)

(52) U.S. Cl.
CPC ........ *A61B 17/3403* (2013.01); *A61B 8/4455* (2013.01); *A61B 17/34* (2013.01); *A61B 2017/3405* (2013.01); *A61B 2017/3413* (2013.01)

(58) Field of Classification Search
CPC ........ A61B 17/3403; A61B 2017/3405; A61B 2017/3407; A61B 2017/3409; A61B 2017/3411; A61B 2017/3413; A61B 17/34; A61B 8/4455; A61B 8/4411; A61B 2017/00477

USPC ......................................................... 600/461
See application file for complete search history.

(56) References Cited

U.S. PATENT DOCUMENTS

| | | | |
|---|---|---|---|
| 2002/0123689 A1* | 9/2002 | Furia ................. | A61B 17/3403 600/461 |
| 2005/0131291 A1* | 6/2005 | Floyd ................ | A61B 17/3403 600/424 |
| 2005/0143753 A1* | 6/2005 | Whitmore, III ...... | A61B 90/11 606/130 |
| 2009/0143684 A1* | 6/2009 | Cermak .............. | A61B 8/4422 600/461 |

(Continued)

OTHER PUBLICATIONS

International Search Report dated Mar. 23, 2017 for PCT/CN2016/090134, international filing dated Jul. 15, 2016.

*Primary Examiner* — Katherine H Schwiker
(74) *Attorney, Agent, or Firm* — Fox Rothschild LLP

(57) ABSTRACT

A needle groove body, a puncture frame body and a puncture frame, wherein the needle groove body is a hollow cylindrical structure, and comprises a first baffle, a first fixing plate, a limiting plate, and a second fixing plate which are connected in sequence. The needle groove body has multiple specifications and can adapt to puncture needles of different specifications in puncture operations; a u-shaped needle groove can be formed between the first baffle of the needle groove body and a second baffle as well as an inclined mounting plate of the puncture frame body so as to accommodate free movement of a puncture needle in the u-shaped needle groove; and the u-shaped needle groove, which is semi-open, can implement a function of needle-frame separation (separation of the puncture needle from the puncture frame) in puncture operations.

16 Claims, 4 Drawing Sheets

(56) References Cited

U.S. PATENT DOCUMENTS

2012/0330159 A1\* 12/2012 Orome ............... A61B 5/15003
600/461
2013/0150714 A1\* 6/2013 Howlett ............... A61B 8/4483
600/439

\* cited by examiner

NEEDLE GROOVE BODY, PUNCTURE FRAME BODY AND PUNCTURE FRAME

RELATED APPLICATIONS AND CLAIM OF PRIORITY

This application is a national stage application of, and claims priority to, International Patent Application No. PCT/CN2016/090134, filed Jul. 15, 2016, the disclosure of which is incorporated herein by reference in its entirety.

TECHNICAL FIELD

The present invention relates to the technical field of ultrasonic B-ultrasound puncture operation tools, and specifically relates to a needle groove body, a puncture frame body and a puncture frame.

BACKGROUND

The current in vitro puncture frames generally control the needle insertion in two ways: 1. using a rotating needle groove structure; and 2. using a single needle groove body structure, wherein individual needle groove bodies all have thicknesses of different specifications for one-to-one correspondence to puncture needles, so each puncture frame body using the single needle groove body structure must be equipped with needle groove bodies of various specifications. In B-ultrasound puncture operations, the doctor would select, according to the clinical use, needle groove bodies of different specifications for the B-ultrasound operations. At present, the needle groove bodies of the existing structures, which are complicated in installation and disassembly, cannot accomplish the purpose of simple operation, thereby increasing the difficulty of the doctor's operation during puncture operations.

SUMMARY

In order to overcome those technical defects in the prior art, i.e., complicated installation and disassembly of the needle groove body and the puncture frame body and an increased difficulty of the doctor's operation during puncture operations, the present invention provides a needle groove body that is simple in structure and convenient in installation and disassembly, a puncture frame body for use together with the needle groove body, and a puncture frame consisting of the needle groove body and the puncture frame body, which are capable of allowing the doctor to operate with one hand, thereby reducing the difficulty of the doctor's operation during puncture operations.

In order to achieve the above purpose, the technical solution adopted by the present invention is:

a needle groove body, which is a hollow cylindrical structure, and comprises a first baffle, a first fixing plate, a limiting plate, and a second fixing plate which are connected in sequence.

The needle groove body, which has a simple structure, can facilitate its installation and disassembly with and from a mating puncture frame body.

Preferably, a boss is provided in a central portion at one end of the first fixing plate.

Preferably, the first fixing plate is provided with u-shaped connecting grooves al positions on both sides of the boss.

Preferably, the second fixing plate is provided with two n-shaped engaging grooves.

A puncture frame body for use together with a needle groove body according to any one of the above, wherein the puncture frame body has a connecting portion at one end, and the connecting portion is provided with a second baffle and an inclined mounting plate which are perpendicular to each other, wherein the inclined mounting plate is provided with a first rib position and a second rib position which are parallel to each other.

Preferably, two hooks are provided at a top end on one side of the first rib position away from the second rib position, for catching the needle groove body.

Preferably, a reinforcing rib is provided at a bottom end on one side of the first rib position close to the second rib position, so as too enhance elastic feel in the hand.

Preferably, two limiting ribs are provided at a bottom end on one side of the second rib position away from the first rib position. The limiting ribs, which cooperate with the n-shaped engaging grooves on the needle groove body, can catch the needle groove body so that the needle groove body does not shake.

A puncture frame, comprising one or more needle groove bodies according to any one of the above and a puncture frame body according to any one of the above.

Preferably, there are a plurality of needle groove bodies, and the first baffles of the plurality of needle groove bodies are different in thickness. When the puncture frame body is used in cooperation with needle groove bodies of different specifications, the spacing between the first baffle and the second baffle would be changed to adapt to puncture needles of different specifications.

The present invention has the following advantageous effects:

the needle groove body has multiple different specifications and can adapt to puncture needles of different specifications in puncture operations;

the needle groove body is easy and convenient to fix and replace, easy to operate, and capable of allowing the doctor to operate with one hand;

a u-shaped needle groove can be formed between the first baffle of the needle groove body and the second baffle as well as the inclined mounting plate of the puncture frame body so as to accommodate free movement of a puncture needle in the u-shaped needle groove; and the u-shaped needle groove, which is semi-open, can implement a function of needle-frame separation (separation of the puncture needle from the puncture frame) in puncture operations at any time.

BRIEF DESCRIPTION OF THE DRAWINGS

FIGS. 2-1 to 2-3 are all views of the needle groove bodies viewed from the direction of a first fixing plate (which are needle groove bodies of three thickness specifications, respectively);

FIG. 3 is a structural schematic diagram of a puncture frame body according to an embodiment of the present invention;

In the figures, 1—needle groove body; 11—first baffle; 12—first fixing plate; 121—boss; 122—u-shaped connecting groove; 123—first indicator arrow; 124—model mark;

13—limiting plate; 14—second fixing plate; 141—n-shaped engaging groove; 2—connecting portion; 21—second baffle; 22—inclined mounting plate; 23—first rib position; 231—hook; 232—reinforcing rib; 233—second indicator arrow; 24—second rib position; 241—limiting rib; 3—u-shaped needle groove.

DETAILED DESCRIPTION

Hereinafter, the structures of the present invention will be explained in detail with reference to the figures.

Figure 1:
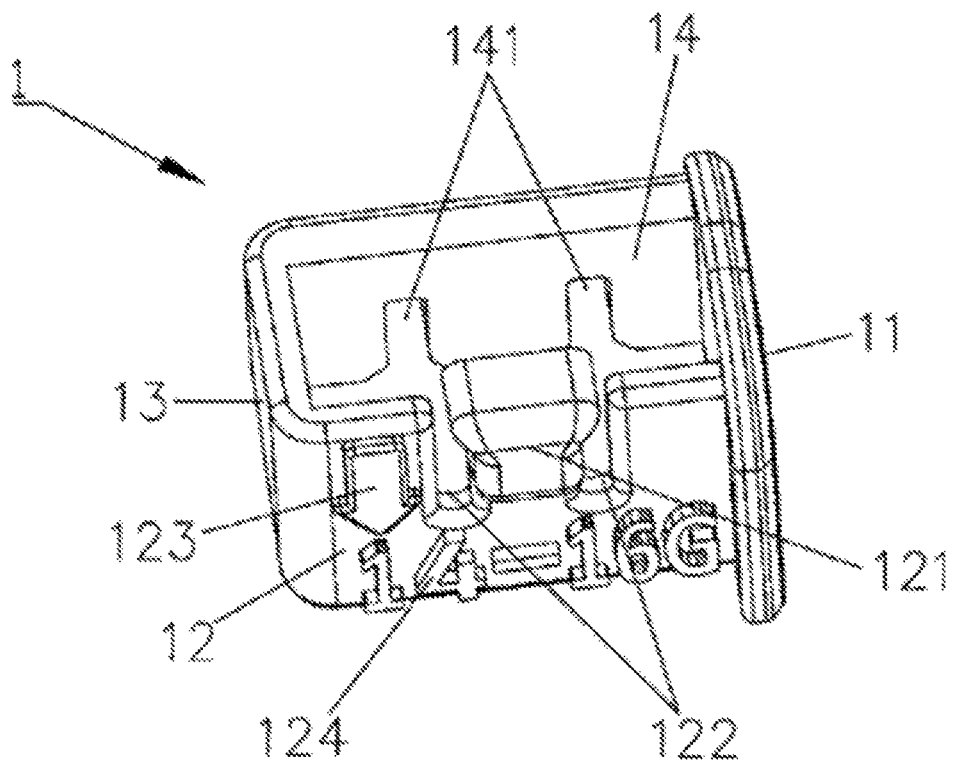
FIG. 1 is a structural schematic diagram of a needle groove body according to an embodiment of the present invention.
Figures 1, 2:
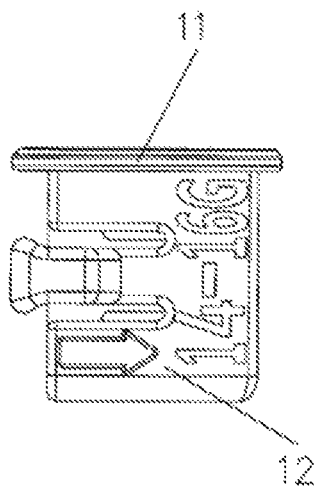
Figure 2:
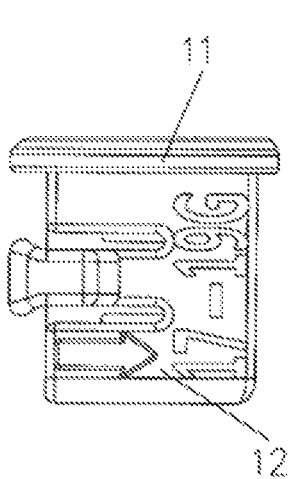
Figures 2, 3:
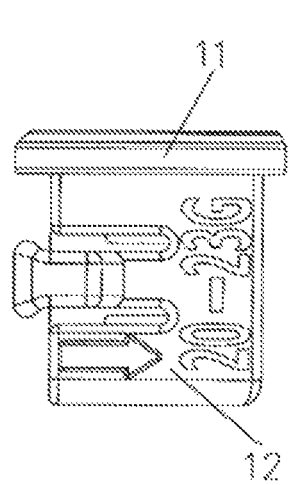
Figure 3:
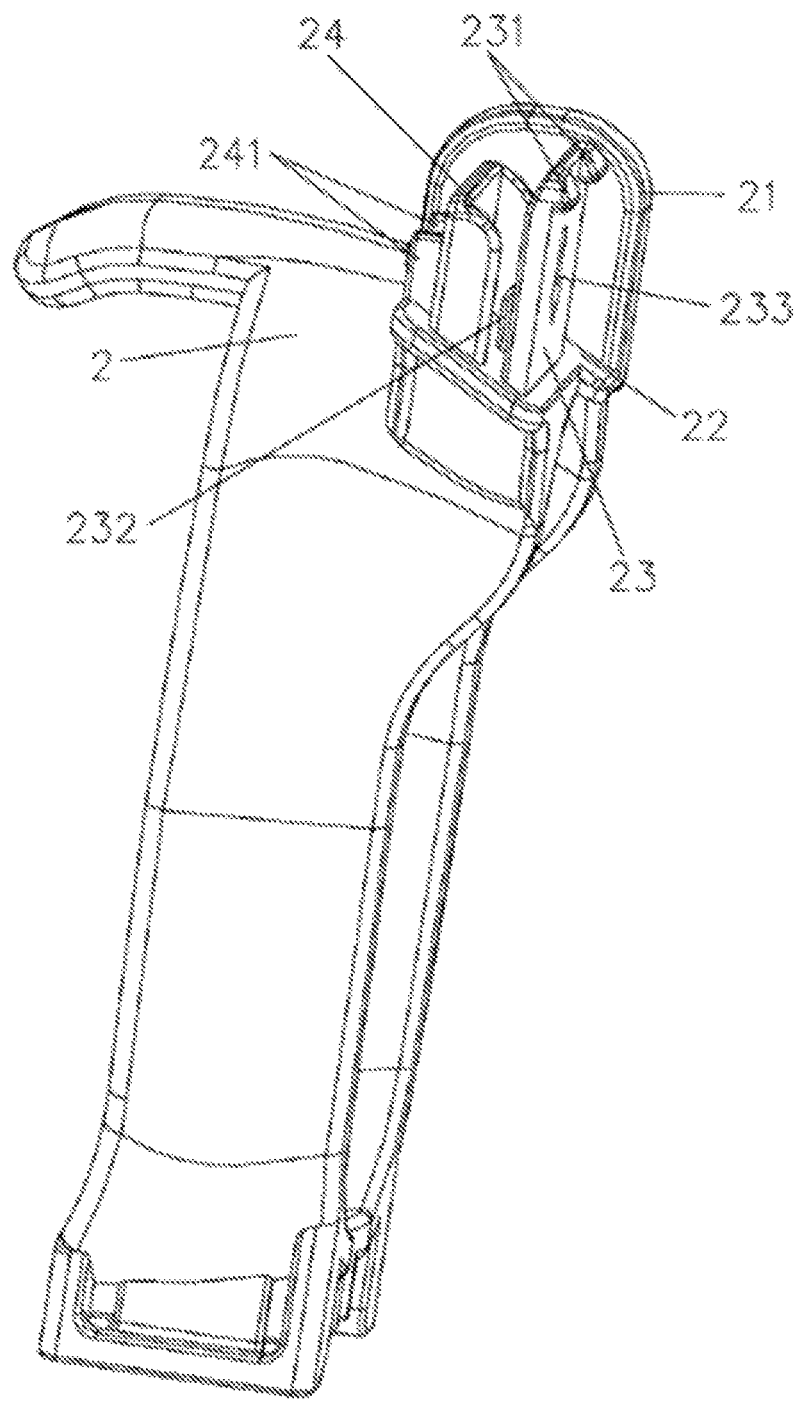

As shown in FIG. 1 and FIGS. 2-1 to 2-3, a needle groove body 1 provided by an embodiment of the present invention is a hollow cylindrical structure, and consists of a first baffle 11, a first fixing plate 12, a limiting plate 13, and a second fixing plate 14 which are connected in sequence, wherein the first baffle 11 can be designed in a variety of thickness specifications.

In the needle groove body 1 provided by the embodiment of the present invention, the first baffle 11 and the limiting plate 13 are parallel to each other, and the first fixing plate 12 and the second fixing plate 14 are parallel to each other.

In the needle groove body 1 provided by the embodiment of the present invention, a boss 121 is provided in a central portion at one end of the first fixing plate 12. The first fixing plate 12 is provided with u-shaped connecting grooves 122 at positions on both sides of the boss 121. The first fixing plate 12 is further provided with a first indicator arrow 123 "↓" and a model mark 124 for promptly indicating the specification of a needle in use. The second fixing plate 14 is provided with two n-shaped engaging grooves 141.

As shown in FIG. 3, a puncture frame body for use together with the above needle groove body 1, as provided by an embodiment of the present invention, has a connecting portion 2 at one end, and the connecting portion 2 is provided with a second baffle 21 and an inclined mounting plate 22 which are perpendicular to each other, wherein an upper surface of the inclined mounting plate 22 is a needle insertion start plane, and the inclined mounting plate 22 can be fitted with the bottom of the needle groove body 1.

In the puncture frame body for use together with the above needle groove body 1, as provided by the embodiment of the present invention, the inclined mounting plate 22 is provided with a first rib position 23 and a second rib position 24 which are parallel to each other and cooperate with the first fixing plate 12 and the second fixing plate 14, respectively, wherein the needle groove body 1 can be sleeved outside the first rib position 23 and the second rib position 24.

In the puncture frame body for use together with the above needle groove body 1, as provided by the embodiment of the present invention, two hooks 231 are provided at a top end on one side of the first rib position 23 away from the second rib position 24, for catching the needle groove body 1. A reinforcing rib 232 is provided at a bottom end on one side of the first rib position 23 close to the second rib position 24, and can enhance elastic feel in the hand. A second indicator arrow 233 "↓" is further provided in a central portion on one side of the first rib position 23 away from the second rib position 24.

In the puncture frame body for use together with the above needle groove body 1, as provided by the embodiment of the present invention, two limiting ribs 241, which are provided at a bottom end on one side of the second rib position 24 away from the first rib position 23, cooperate with the two n-shaped engaging grooves 141, respectively. The limiting ribs 241, which are engaged with the n-shaped engaging grooves 141 on the needle groove body 1, can catch the needle groove body 1 so that the needle groove body 1 does not shake.

Figure 4:
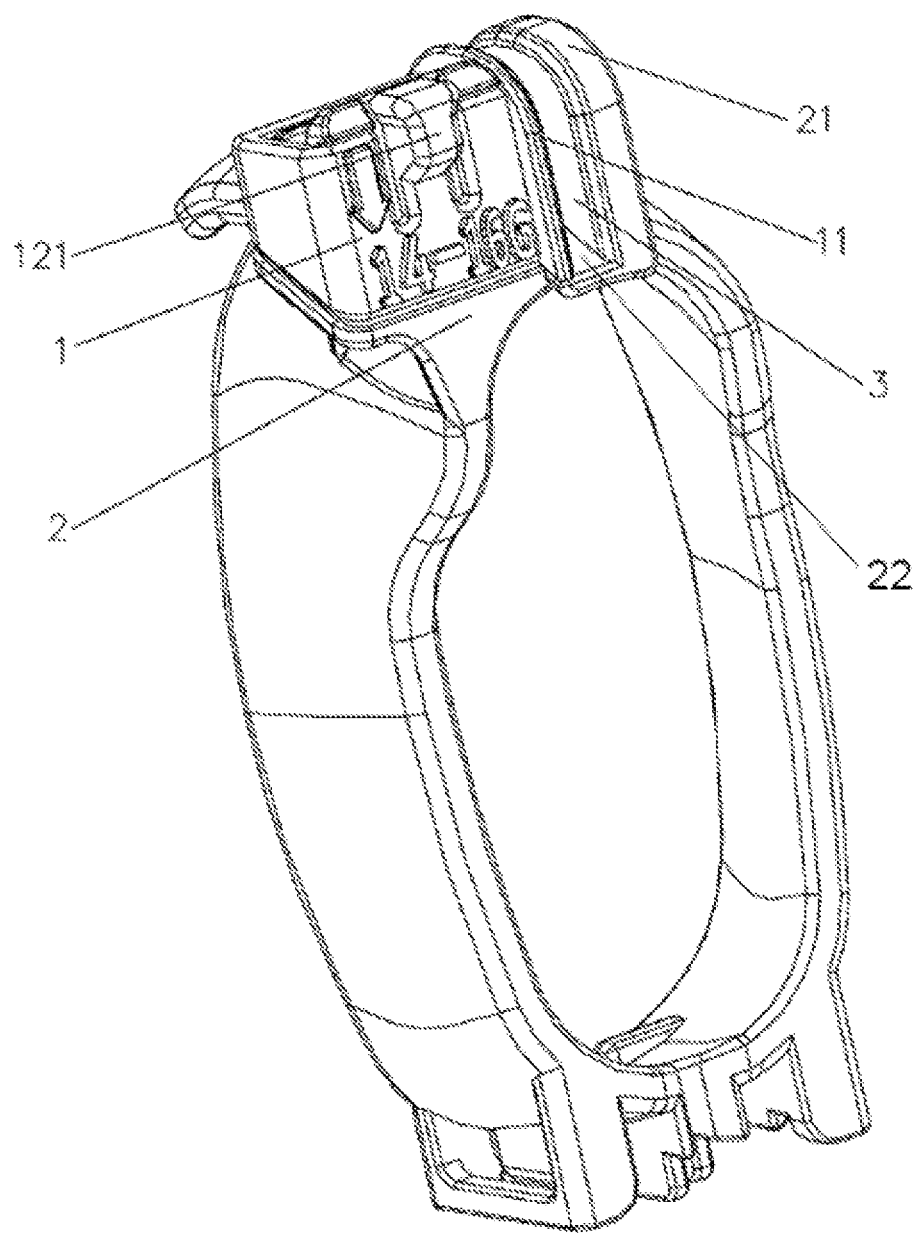
FIG. 4 is a structural schematic diagram of a puncture frame according to an embodiment of the present invention.
Figure 5:
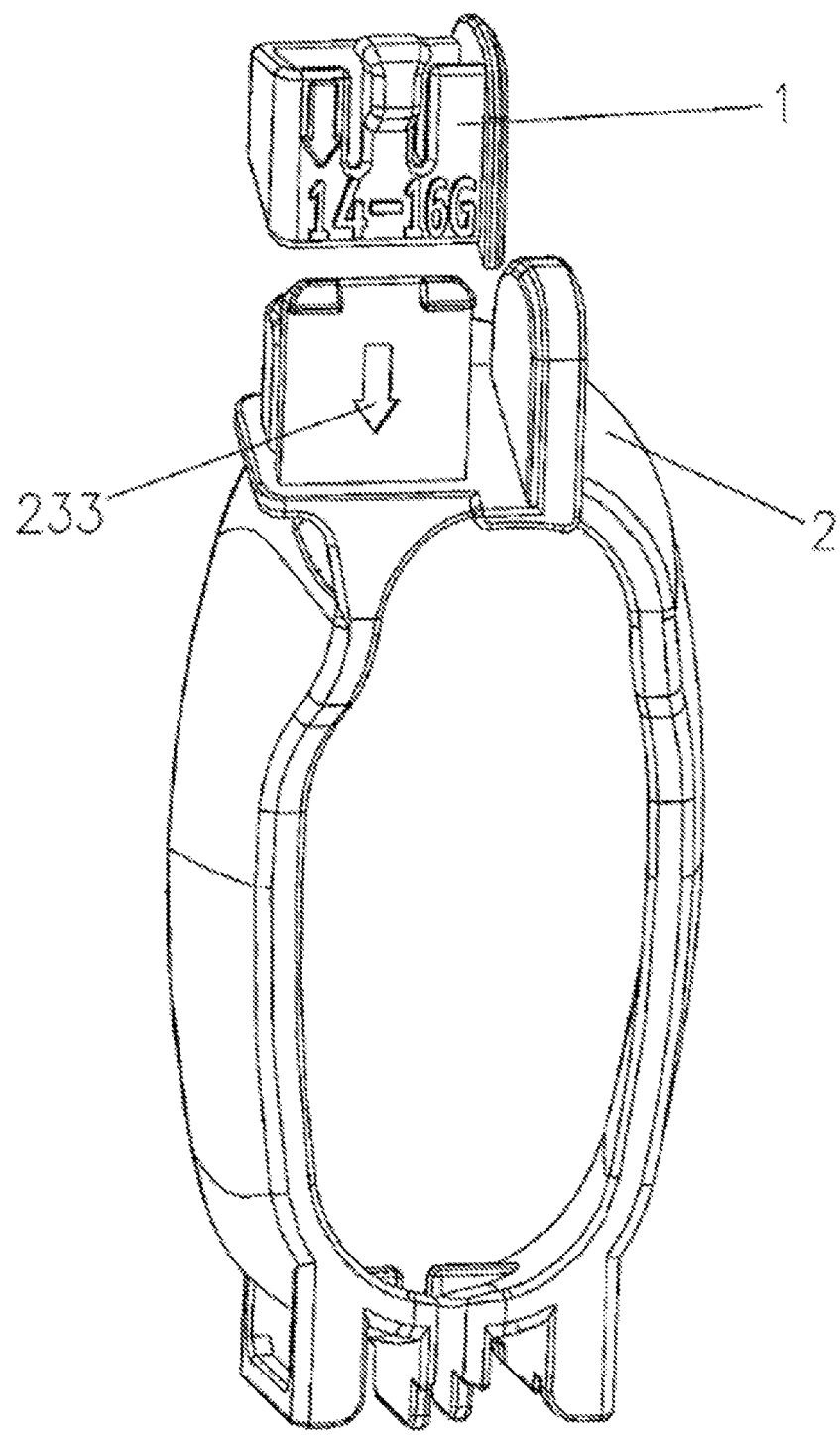
FIG. 5 is an exploded view of the puncture frame according to the embodiment of the present invention.

As shown in FIGS. 4 to 5, a puncture frame provided by an embodiment of the present invention comprises a plurality of the above needle groove bodies 1 and one of the above puncture frame bodies. The first baffles 11 of the plurality of needle groove bodies 1 are different in thickness. When the puncture frame body is used in cooperation with needle groove bodies 1 of different thickness specifications, the spacing between the first baffle 11 and the second baffle 21 would be changed to adapt to puncture needles of different specifications.

The puncture frame provided by the embodiment of the present invention can be implemented according to the following operation steps in specific use:

After the puncture frame body is fixed to an ultrasonic B-ultrasound probe, the needle groove body 1 of a suitable specification is selected, and the side marked with the first indicator arrow 123 "↓" provided on the selected needle groove body 1 is placed in the same direction as the second indicator arrow 233 "↓" provided on the puncture frame body and is pressed down along a direction indicated by the second indicator arrow 233 "↓" on the puncture frame body. At this time, the two hooks 231 provided on the first rib position 23 are deformed. When the needle groove body 1 is pushed into position (the bottom end of the needle groove body 1 is completely fitted with the inclined mounting plate 22), the two hooks 231 are elastically returned to clamp the needle groove body 1 on the puncture frame body for fixation, and after hearing a "snap" sound, this indicates that it has been installed in place. The two limiting ribs 241 provided on the second rib position 24 are engaged with the two n-shaped engaging grooves 141 provided on the needle groove body 1 to catch the needle groove body 1 so that it does not shake. At this time, a free open u-shaped needle groove 3 is formed between the first baffle 11 of the needle groove body 1 and the second baffle 21 as well as the inclined mounting plate 22 of the puncture frame body, and, in a B-ultrasound puncture operation, the puncture needle can be freely inserted at any angle into the formed free open u-shaped needle groove 3. When the puncture needle specification needs to be changed during an operation, the structure of the boss 121 provided on the needle groove body 1 is pinched and pressed inward until it stops, such that the two hooks 231 are separated from the needle groove body 1; the needle groove body 1 is lifted upward and taken out for a replacement with a needle groove body 1 of the required specification. The difference between the needle groove bodies 1 of different specifications lies in the wall thickness of the first baffle 11 provided on the needle groove body 1, so that the spacing between the first baffle 11 and the second baffle 21 (i.e., the width of the u-shaped needle groove 3) can be adjusted, for the convenience of the operation.

The above are only preferred embodiments of the present invention and are not intended to limit the present invention. Any modifications, equivalent substitutions, simple improvements and the like made in the essential contents of the present invention shall be included in the scope of protection of the present invention.

The invention claimed is:

1. A needle groove body and a puncture frame body to be fixed to an ultrasonic probe during a puncture operation, comprising:

the needle groove body, having a substantially rectangular close-ended frame structure and comprising:

a first baffle, a first fixing plate, a limiting plate, and a second fixing plate,
  wherein the first baffle, the first fixing plate, the limiting plate, and the second fixing plate are all connected in sequence and function as respective four sides of the substantially rectangular frame structure; and
the puncture frame body, comprising:
  a connecting portion at an end of the puncture frame body, into which end the needle groove body is installable,
    wherein the connecting portion is provided with a second baffle and an inclined mounting plate, and the second baffle is perpendicular to the inclined mounting plate, such that the first baffle, the second baffle and the inclined mounting plate can form a u-shaped needle groove for accommodating a movement of a puncture needle.

2. The needle groove body according to claim 1, further comprising a boss that is provided in a central portion at one end of the first fixing plate.

3. The needle groove body according to claim 2, wherein:
the first fixing plate is provided with two u-shaped connecting grooves; and
one of the two u-shaped connecting grooves is located on one side of the boss and the other one of the two u-shaped connecting grooves is located on an other side of the boss.

4. The needle groove body according to claim 1, wherein the second fixing plate is provided with two n-shaped engaging grooves.

5. A puncture frame body together with a needle groove body, comprising:
the needle groove body that:
  has a substantially rectangular close-ended frame structure,
  is insertable into the puncture frame body to be fixed to an ultrasonic probe during a puncture operation, and
  comprises a first baffle, a first fixing plate, a limiting plate, and a second fixing plate which are all connected in sequence and function as respective four sides of the substantially rectangular close-ended frame structure of the needle groove body; and
the puncture frame body, comprising:
  a connecting portion at an end of the puncture frame body where the needle groove body is installable,
  wherein the connecting portion is provided with a second baffle and an inclined mounting plate, and the second baffle is perpendicular to the inclined mounting plate such that the first baffle, the second baffle and the inclined mounting plate form a u-shaped needle groove for accommodating a movement of a puncture needle, and
  wherein the inclined mounting plate is provided with a first rib position and a second rib position, and the first rib position is parallel to the second rib position.

6. The puncture frame body according to claim 5, further comprising two hooks that are provided at a top end on one side of the first rib position away from the second rib position.

7. The puncture frame body according to claim 5, further comprising a reinforcing rib that is provided at a bottom end on one side of the first rib position close to the second rib position.

8. The puncture frame body according to claim 5, further comprising two limiting ribs that are provided at a bottom end on one side of the second rib position away from the first rib position.

9. A puncture frame to be fixed to an ultrasonic probe during a puncture operation, the puncture frame comprising:
one or more needle groove bodies, wherein each of the one or more needle groove bodies:
  has a substantially rectangular close-ended frame structure,
  is installable into a puncture frame body to be fixed to an ultrasonic probe during a puncture operation, and
  comprises a first baffle, a first fixing plate, a limiting plate, and a second fixing plate which are all connected in sequence and function as respective four sides of the substantially rectangular close-ended frame structure of the needle groove body; and
the puncture frame body, comprising:
  a connecting portion at an end of the puncture frame body where the needle groove body is installable,
  wherein:
    the connecting portion is provided with a second baffle and an inclined mounting plate, and the second baffle is perpendicular to the inclined mounting plate, such that the first baffle, the second baffle and the inclined mounting plate can form a u-shaped needle groove for accommodating a movement of a puncture needle, and
    the inclined mounting plate is provided with a first rib position and a second rib position, and the first rib position is parallel to the second rib position.

10. The puncture frame according to claim 9, wherein the one or more needle groove bodies comprise a plurality of needle groove bodies, and the first baffles of the plurality of needle groove bodies are different in a thickness.

11. The puncture frame according to claim 9, wherein each of the one or more needle groove bodies further comprises a boss that is provided in a central portion at one end of the first fixing plate of the needle groove body.

12. The puncture frame according to claim 11, wherein, for each of the one or more needle groove bodies, the first fixing plate is provided with two u-shaped connecting grooves, one of the two u-shaped connecting groves is located on one side of the boss, and the other of the two u-shaped connecting groves is located on an other side of the boss.

13. The puncture frame according to claim 9, wherein, for each of the one or more needle groove bodies, the second fixing plate is provided with two n-shaped engaging grooves.

14. The puncture frame according to claim 9, further comprising two hooks that are provided at a top end on one side of the first rib position away from the second rib position.

15. The puncture frame according to claim 9, further comprising a reinforcing rib provided at a bottom end on one side of the first rib position close to the second rib position.

16. The puncture frame according to claim 9, further comprising two limiting ribs that are provided at a bottom end on one side of the second rib position away from the first rib position.

* * * * *